US00PP37823P2

(12) United States Plant Patent
Smith

(10) Patent No.: US PP37,823 P2
(45) Date of Patent: Oct. 27, 2026

(54) ***CHRYSANTHEMUM* PLANT NAMED 'CIFZ0124'**

(50) Latin Name: ***Chrysanthemum* x *morifolium***
Varietal Denomination: CIFZ0124

(71) Applicant: SYNGENTA CROP PROTECTION AG, Basel (CH)

(72) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 19/443,076

(22) Filed: Jan. 8, 2026

(51) Int. Cl.
*A01H 5/02* (2018.01)
*A01H 6/14* (2018.01)

(52) U.S. Cl.
USPC ..... Plt./287

(58) Field of Classification Search
USPC ..... Plt./287, 291, 292
CPC ..... A01H 5/02; A01H 5/00; A01H 6/1424; A01H 6/14
See application file for complete search history.

(56) References Cited

U.S. PATENT DOCUMENTS

PP35,056 P2 * 3/2023 Smith ..... A01H 6/1424 Plt./292

* cited by examiner

*Primary Examiner* — June Hwu
(74) *Attorney, Agent, or Firm* — Dale Skalla

(57) ABSTRACT

A new garden type *Chrysanthemum* plant named 'CIFZ0124', particularly distinguished by its medium size plant with round plant habit, a medium size decorative flower, purple flower color and a natural season response late September.

1 Drawing Sheet

Latin name of the genus and species of the plant claimed: *Chrysanthemum* x *morifolium.*
Varietal denomination: 'CIFZ0124'.

BACKGROUND OF THE NEW PLANT

The present invention comprises a new *Chrysanthemum*, botanically known as *Chrysanthemum* x *morifolium*, and hereinafter referred to by the variety name 'CIFZ0124'.

'CIFZ0124' is a product of a planned breeding program. The new cultivar has medium size plant with round plant habit, a medium size decorative flower, purple flower color and a natural season response late September.

'CIFZ0124' originated from a mutation of X-ray treated cuttings in October 2022 in Fort Myers, Florida. 'CIFZ0124' was selected from the resulting plants on Apr. 17, 2023 in Alva, Florida The sport parent was a proprietary seedling, 'FE0070-2', a dark lavender decorative.

TABLE 1

Characteristics of the sport parent, compared to 'CIFZ0124':

| | 'CIFZ0124' | 'FE0070-2' |
|---|---|---|
| Natural response: | 2-3 days later | 2-3 days earlier |
| Blackcloth response: | 2 days later | 2 days earlier |
| Flower color: | Darker | Lighter |

As the new variety is the result of mutation breeding, there is not a male parent.

The first act of asexual reproduction of 'CIFZ0124' was accomplished when vegetative cuttings were propagated from the initial selection in May 2023 in Alva, Florida.

BRIEF SUMMARY OF INVENTION

Horticultural examination of plants grown from cuttings of the plant initiated in May 2023 and continuing thereafter, has demonstrated that the combination of characteristics as herein disclosed for 'CIFZ0124' are firmly fixed and are retained through successive generations of asexual reproduction.

'CIFZ0124' has not been observed under all possible environmental conditions. The phenotype may vary significantly with variations in environment such as temperature, light intensity and day length.

A Plant Breeder's Right for this cultivar has not yet been applied for. 'CIFZ0124' has not been made publicly available prior to the effective filing date of this application, notwithstanding any disclosure that may have been made less than one year prior to the effective filing date of this application by the inventor or another who obtained 'CIFZ0124' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIFZ0124' with colors being as true as possible with an illustration of this type.

Figure 1:
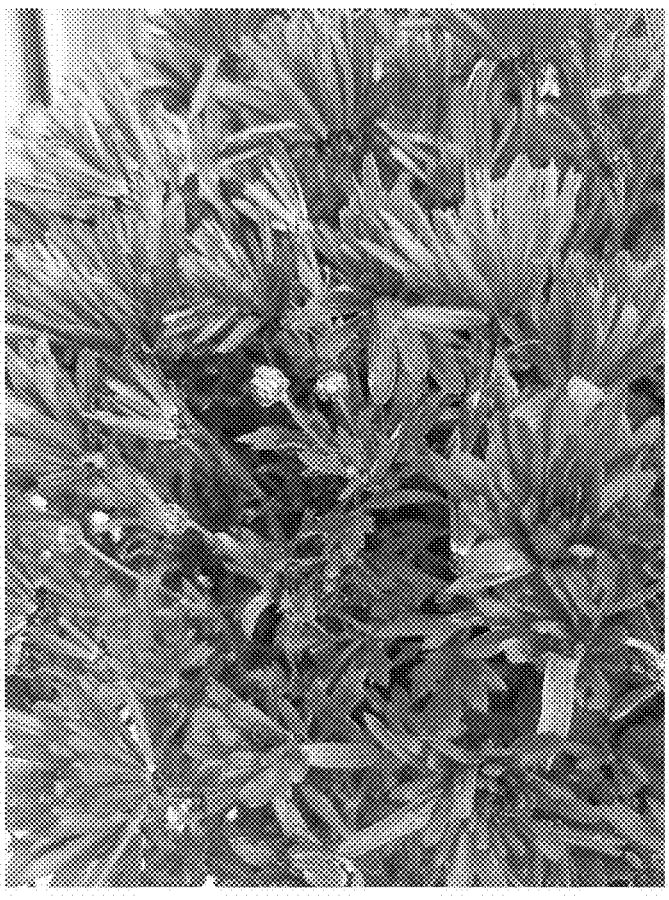
Figure 2:
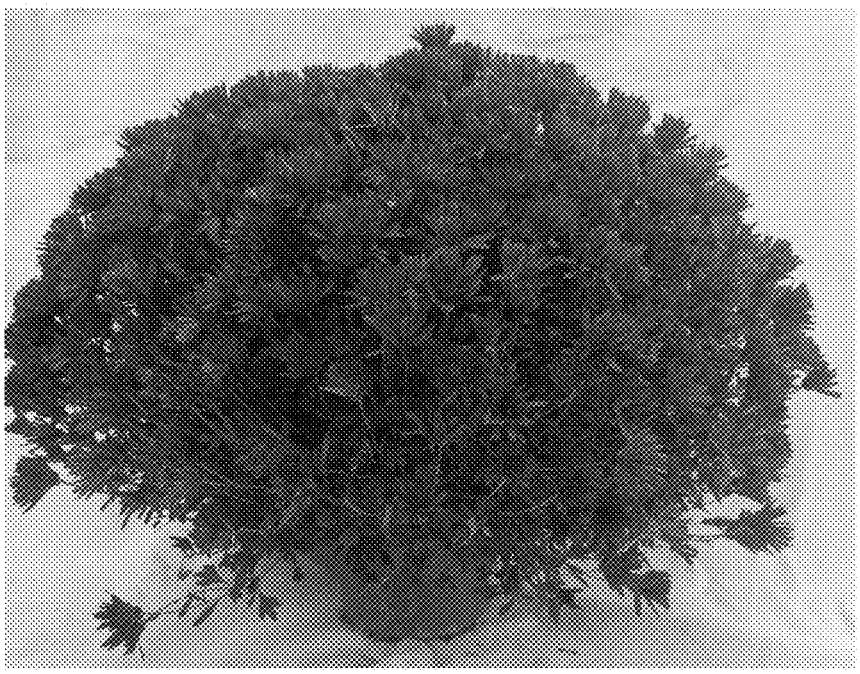

The photographic drawings show in FIG. 1 a close view of flower of the new variety and in FIG. 2 a flowering plant from an outdoor trial.

The aforementioned photographs: FIG. 1, as well as FIG. 2 were taken on Oct. 22, 2025 both showing a plant from the same outdoor trial (natural day length with night interruption during rooting phase) in Enkhuizen, The Netherlands.

These plants were about 19 weeks of age. One cutting, rooted under night interruption per pot had been planted in a 19 cm pot, not pinched in week 23. Plants started flowering early October 2025.

The measurements were taken in Enkhuizen, The Netherlands in October 2025 on plants from the same outdoor trial.

DETAILED BOTANICAL DESCRIPTION

Color references are made to The Royal Horticultural Society Colour Chart (R.H.S.) 2001.

TABLE 2

DIFFERENCES BETWEEN THE NEW VARIETY 'CIFZ0124' AND TWO MOST SIMILAR VARIETIES:

| Trait | 'CIFZ0124' | 'CIFZ0109', U.S. Plant Pat. No. 36,552 |
|---|---|---|
| Blackcloth response: | 2 days slower | 2 days faster |
| Flower size: | Bit larger | Bit smaller |
| Plant size: | Bit larger | Bit smaller |
| Flowering uniformity: | Less uniform | More uniform |
| Flower color longevity: | 1/2 week more | 1/2 week less |

TABLE 3

| | 'CIFZ0124' | 'GED18ARL6V', U.S. Plant Pat. No. 30,363 |
|---|---|---|
| Flower size: | Smaller | Larger |
| Flowering uniformity: | Less uniform | More uniform |
| Flower color longevity: | 1.5 times longer lasting | 1/3 less longevity |

Plant:

*Form, growth and habit.*—Herbaceous garden-type, stems upright and outwardly spreading, freely branching.

*Plant height (above soil).*—34 cm.

*Plant height (inflorescence included).*—38 cm.

*Plant width.*—60 cm.

Roots:

*Number of days to initiate roots.*—About 4 days at about 22° C.

*Number of days to produce a rooted cutting.*—14-16 days at 22° C.

*Type.*—Fine, fibrous, free branching.

*Color.*—RHS N155B.

Foliage:

*Arrangement.*—Alternate.

*Immature leaf, color upper surface.*—RHS 137B.

*Immature leaf, color lower surface.*—RHS 147C.

*Mature leaf, color, upper surface.*—RHS 137A.

*Mature leaf, color lower surface.*—RHS 147B.

*Length.*—4.5 cm.

*Width.*—2.5 cm.

*Shape.*—Ovate, with distinct lobes.

*Base shape.*—Attenuate.

*Apex shape.*—Apiculate.

*Margin.*—3 lobed.

*Number of margin indentations.*—6-10.

*Depth of margin indentations.*—2-4 mm.

*Leaf length terminal lobe relative to total leaf length.*—1:2.

*Length of terminal leaf lobe in relation to the leaf length.*—Long.

*Leaf depth lower lateral sinus.*—1.2 cm.

*Depth of lowest lateral leaf sinus.*—Medium.

*Texture, upper surface.*—Bifid hairs.

*Texture, lower surface.*—Bifid hairs.

*Color of veins, upper surface.*—RHS 138B.

*Color of veins, lower surface.*—RHS 138B.

*Pattern of veining.*—Palmate.

*Petiole color.*—RHS 138B.

*Petiole length.*—1.0 cm.

*Petiole orientation.*—Horizontal to moderately upwards.

*Diameter.*—0.2 cm.

*Texture.*—Bifid hairs.

*Presence of stipules.*—No.

Stem:

*Quantity of main branches per plant.*—6-8.

*Color of stem.*—RHS 138B with spots RHS N79B near base.

*Length of stem.*—8-10 cm.

*Diameter.*—0.3 cm.

*Length of internodes.*—0.5-2.5 cm.

*Texture.*—Bifid hairs.

*Color of peduncle.*—Variable; some peduncles RHS N79B towards flower and RHS 138B at base, others only RHS 138B for whole peduncle.

*Length of peduncle.*—5.0-7.0 cm.

*Peduncle diameter.*—0.2 cm.

*Texture.*—Bifid hairs.

Inflorescence:

*Type.*—Compositae, solitary, decorative inflorescences borne terminally above foliage, ligulate ray florets arranged in whorls on a capitulum giving a double flower.

*Quantity of short days to flowering (response time).*—Approximately 7.5 weeks.

*Quantity of inflorescences per plant.*—About 750 with some small buds developing.

*Lastingness of individual blooms on the plant.*—About five weeks from first color.

*Fragrance.*—Slightly spicy.

Bud (when showing color):

*Color.*—RHS N79C.

*Length.*—0.8 cm.

*Width.*—0.7 cm.

*Shape.*—Oblate.

Immature inflorescence (at moment of opening):

*Diameter.*—1.8 cm.

*Color of ray florets, upper surface.*—RHS N79C.

*Color of ray florets, lower surface.*—RHS N79C.

Mature inflorescence:

*Diameter.*—3.5 cm.

*Depth.*—2.7 cm.

*Total diameter of disc.*—0 cm.

*Receptacle color.*—RHS 138A.

*Receptacle height.*—0.7 cm.

*Receptacle diameter.*—1.0 cm.

*Length of corolla tube.*—No tube.

Ray florets:
*Average quantity of florets.*—90.
*Number of whorls.*—7-9.
*Color of florets, upper surface.*—RHS N79C.
*Color lower surface.*—RHS N79C.
*Length.*—2.9 cm.
*Width/diameter.*—0.4 cm.
*Shape.*—Oblanceolate.
*Apex shape.*—Dentate.
*Base shape.*—Strongly concave.
*Margin.*—Entire.
*Margin.*—Type of rolling Moderately involute.
*Texture, upper surface.*—Papillate.
*Lower surface.*—Papillate.
*Ribs present.*—Yes.
*Number of keels.*—1.
*Profile at widest point.*—Weakly to moderately concave.
*Longitudinal axis shape.*—Straight.
*Longitudinal axis curvature strength.*—No curvature.
*Corolla tube shape.*—No tube.

Disc florets:
*Number of disc florets.*—0.

Inflorescence (at moment of senescence):
*Color of ray florets, upper surface.*—RHS N79C.
*Color of ray florets, lower surface.*—RHS N79C.

Phyllaries:
*Quantity.*—36.
*Color, upper surface.*—RHS 137A.
*Color, lower surface.*—RHS 147B.
*Length.*—0.2-0.4 cm.
*Width.*—0.1 cm.
*Shape.*—Ensiform.
*Apex shape.*—Acute.
*Base.*—Fused.
*Margins.*—Entire.
*Texture, upper surface.*—Glabrous.
*Texture, lower surface.*—Canescent.

Reproductive organs:
*Pistil.*—One.
*Length.*—0.4 cm.
*Style color.*—RHS 1B.
*Style length.*—0.3 cm.
*Stigma color.*—RHS 16A.
*Stigma shape.*—Bi-parted.
*Ovary color.*—RHS 150D.
*Ovary length.*—0.2 cm.
*Ovary width.*—0.1 cm.

Androecium: No androecium present, as these are only present on disc florets.

Seed set: No seed set observed.

Disease and pet resistance susceptibility: Has not been determined.

What is claimed is:

1. A new and distinct variety of *Chrysanthemum* plant named 'CIFZ0124' substantially as illustrated and described herein.

* * * * *